United States Patent
Axe et al.

(10) Patent No.: US 6,609,410 B2
(45) Date of Patent: Aug. 26, 2003

(54) HIGH STRAIN RATE TESTER FOR MATERIALS USED IN SPORTS BALLS

(75) Inventors: John D. Axe, Lecanto, FL (US); Vincent J. Simonds, Brimfield, MA (US); Thomas A. Veilleux, Charlton, MA (US)

(73) Assignee: Spalding Sports Worldwide, Inc., Chicopee, MA (US)

( * ) Notice: Subject to any disclaimer, the term of this patent is extended or adjusted under 35 U.S.C. 154(b) by 0 days.

(21) Appl. No.: 09/965,039

(22) Filed: Sep. 26, 2001

(65) Prior Publication Data

US 2002/0053232 A1 May 9, 2002

Related U.S. Application Data

(60) Provisional application No. 60/236,459, filed on Sep. 29, 2000.

(51) Int. Cl.[7] .................................................. G01N 3/32
(52) U.S. Cl. ................................................... 73/12.04
(58) Field of Search ........................... 73/12.01, 12.02, 73/12.04, 12.05, 12.06, 12.07, 12.08, 12.09

(56) References Cited

U.S. PATENT DOCUMENTS

| | | | |
|---|---|---|---|
| 4,292,835 A | * 10/1981 | Bickford | 73/1.15 |
| 5,092,179 A | 3/1992 | Ferguson | |
| 5,520,057 A | 5/1996 | Nakamura | |
| 5,677,494 A | * 10/1997 | Keener et al. | 73/810 |
| 5,739,411 A | 4/1998 | Lee et al. | |
| 6,142,010 A | * 11/2000 | Merck, et al. | 73/81 |
| 6,365,890 B1 | * 4/2002 | Nedderman, Jr. | 250/227.14 |
| 6,389,876 B1 | * 5/2002 | Tanimura et al. | 73/12.01 |

* cited by examiner

*Primary Examiner*—Hezron Williams
*Assistant Examiner*—Corey D. Mack

(57) ABSTRACT

A high strain rate tester for elastomeric materials used in sports balls includes a base on which a sample of the material is mounted and a striker which delivers an impact to the sample, preferably in the vertical direction. A load cell adjacent to the sample measures the reaction force of the impact from the sample and an optical detector measures the displacement of the sample in the vertical direction. The force and displacement measurements are processed to determine the time dependent strain of the material.

16 Claims, 2 Drawing Sheets

HIGH STRAIN RATE TESTER FOR MATERIALS USED IN SPORTS BALLS

This application claims the benefit of U.S. Provisional Application No. 60/236,459 filed on Sep. 29, 2000.

BACKGROUND OF THE INVENTION

In testing and improving sports balls such as basketballs, baseballs, softballs, tennis balls, and golf balls, it is important to understand the impact behavior of the ball. For example, to understand the impact behavior of a golf ball when struck by a golf club, the impact can be modeled using Finite Element Analysis (FEA). Reliable FEA modeling requires accurate numerical characterization of the nonlinear viscoelastic properties of elastomeric materials at moderately high strains, such as $\epsilon_{max} \approx 0.3$, and high strain rates, such as $d\epsilon_{max}/dt \approx 10^3 sec^{-1}$. This requires measurement of stress/strain for sample specimens undergoing such deformations. Conventional hydraulic testers can easily achieve the required strains. Piezoelectrically driven vibrometers or shaker tables can easily achieve the required strains, but not high strain rates and are not well-suited to a single impact event. The present invention is directed toward a striker device capable of achieving the desired strain and strain rates.

BRIEF DESCRIPTION OF THE PRIOR ART

As noted above, it is known in the art to use hydraulic devices and piezoelectrically driven vibrometers to achieve strains in test materials. The Ferguson U.S. Pat. No. 5,092,179, for example, discloses a material testing system in which a hydraulic ram compressively deforms the specimen and permits specimen deformation and strain rate to be independently controlled. Similarly, the Keener et al. U.S. Pat. No. 5,677,494 discloses a method for high strain-rate testing of specimens using an incremental mechanical loading apparatus.

Impact testing for golf clubs, shafts and the like is disclosed in the U.S. Pat. No. 5,739,411 to Lee et al. A compressed spring is used to drive a hammer against one end of a golf shaft under test. A load cell is used to provide an impact force measurement.

While the prior devices operate satisfactorily, they are not intended for nor capable of measuring strain in an elastic material in response to impact as is important for sports ball analysis.

SUMMARY OF THE INVENTION

Accordingly, it is a primary object of the invention to provide a device for measuring the force and resulting deformation of a sample of material, preferably an elastomeric material, used in sports balls when the force is applied so as to produce a high strain rate in the material. The device includes a base on which the sample is mounted, a striker for delivering an impact to a surface of the sample in a first direction, a load cell for measuring the reaction force of the impact from the sample and an optical detector for measuring displacement of the sample in the first direction. The reaction force and displacement measurements are processed to determine the time dependent strain of the material.

According to a more specific object of the invention, the sample is sandwiched between a lower platen such as a bolt passing through the base and having a head portion on which the sample is placed, and an upper platen. The load cell has an annular configuration and surrounds the bolt shaft below the head and above the top of the base. The striker is dropped on the upper platen and the reaction force from the sample is measured by the load cell.

It is a further object of the invention to provide a plurality of optical detectors around the base. The detectors direct light beams against the underside of the upper platen so that deflection of the head resulting from displacement of the sample upon impact can be detected.

BRIEF DESCRIPTION OF THE FIGURES

Other objects and advantages of the invention will become apparent from a study of the following specification when viewed in the light of the accompanying drawing, in which.

DETAILED DESCRIPTION

The most important component of principal strain over most parts of a sports ball is uniaxial compression ($-\epsilon_x = -\epsilon_y = \frac{1}{2}\epsilon_z, \epsilon_z < 0$), although smaller regions are under some uniaxial extension or (for oblique impacts) pure shear ($-\epsilon_x = \epsilon_y, \epsilon_z = 0$). The present invention focuses only on uniaxial compression, although these considerations may be useful in measuring other strain components as well.

The viscous and nonlinear elastic properties of the materials, while the primary focus of the studies, are corrections to the linear, non-viscous behavior which can be easily calculated. These calculations, which provide the design criteria for the device, are summarized below for a test sample having a right prismatic shape and characterized by the following parameters:

A=cross sectional area
L=thickness
E=Young's Modulus of the material
ρ=mass density
$c=(E/\rho)^{1/2}$=velocity of sound.

Figure 1:
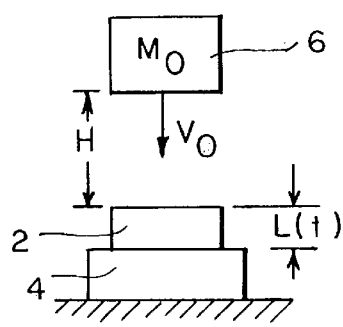
FIG. 1 is a schematic view of a simplified version of a strain rate tester according to the invention.

The basic concept of the strain rate tester according to the invention is shown in FIG. 1. A material sample 2 is placed on a load sensor 4 resting on a fixed support. Sample materials are those used in sports balls including natural and synthetic rubbers such as polybutadiene, thermoplastics, thermoset materials, elastomers, polyurethanes, ionomers, and silicones and combinations thereof. A striker 6 having a mass $M_o$ is dropped from a height H so that it travels freely with a velocity $V_o$. The striker 6 will strike and rebound from the sample 2 in a single compression cycle.

The duration of impact, τ, is long compared with L/c, the time for a sound wave to traverse the sample. The strain state of the sample can then be considered as spatially uniform, and the equation of motion for the striker is $$M o \ddot{x} = \text{force} = -\left(\frac{EA}{L}\right)x = -\left(\frac{\rho A c^2}{L}\right)x$$

where x is the displacement of the sample. The solution with appropriate boundary conditions is $$x(t) = a \sin \omega t; \dot{x}(t) = V(t) = a\omega \cos \omega t,$$

$$\text{where } \omega = \left(\frac{\rho A c^2}{MoL}\right)^{1/2}, 0 < t < \tau, \text{ and } a = \frac{Vo}{\omega}, \tau = \frac{\pi}{\omega}.$$

If A, L, $\rho$ and c are given, the values of $V_o$ and $M_o$ which provide the desired values for $\tau$ and $\epsilon_{max}$ are $$Mo = \frac{\rho A}{L}\left(\frac{c\tau}{\pi}\right)^2, \text{ and } Vo = c\epsilon_{max}\left(\frac{\rho a L}{Mo}\right)^{1/2} = \pi\epsilon_{max}\left(\frac{L}{\tau}\right)$$

Thus the inertial mass of the striker controls the impact time. Once $M_o$ is fixed, $V_o$ controls $\epsilon_{max}$.

The stress/strain relation requires a measurement of the force F(t) and dynamic thickness L(t) of the sample during impact. The drop height H and impact mass $M_o$ are selected to load the material sample 2 at a desired strain rate of 100 to 1,500 in/in per second. Various types of load sensors can be used to measure the reaction force F(t) of the impact and various displacement sensors can be used to measure the deformation, i.e. dynamic thickness L(t) due to impact. Output signals from the load and displacement sensors are recorded in a data acquisition system having a sample rate of from about 100 Hz to 20 GHz.

Figure 2A:
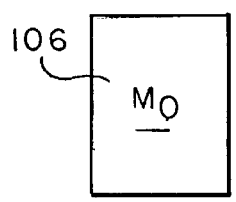
FIGS. 2a–2c are plan views of various strikers according to the invention.
Figure 2B:
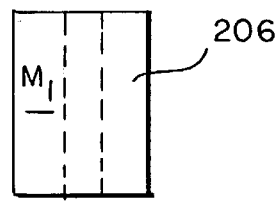
Figure 2C:
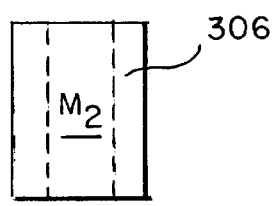

In order to alter the impact in accordance with the size of the sample being tested, different strikers can be used or the height H from which the striker is dropped is altered. In FIGS. 2a–2c are shown different strikers having different masses. The striker 106 in FIG. 2a is solid and thus has a higher mass $M_o$. The striker 206 in FIG. 2b has a through-bore therein and thus has less mass $M_1$ than the striker 106. The striker 306 in FIG. 2c has a larger through-bore and thus less mass $M_2$ than the striker 206. The strikers can have any configuration, but a flat bottom is preferred so that the impact force results solely from the velocity $V_o$ in a vertical direction. Utilizing a striker with a flat bottom results in uniform sample deformation.

Depending on the types of sensors used for measuring displacement, faster moving strikers may be used. For example, if displacement L(t) is measured by high speed imaging, a fast moving striker driven by a hydraulic or spring actuator may be used. If a capacitance type displacement sensor is used, gravity may be sufficient to provide the required velocity $V_o$.

Figure 3:
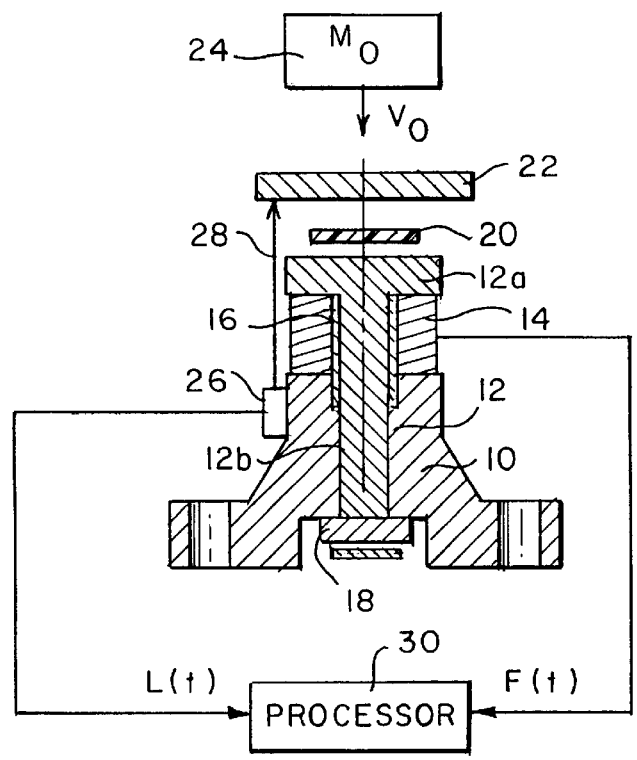
FIG. 3 is a sectional view of a strain rate tester according to a preferred embodiment of the invention.
Figure 4:
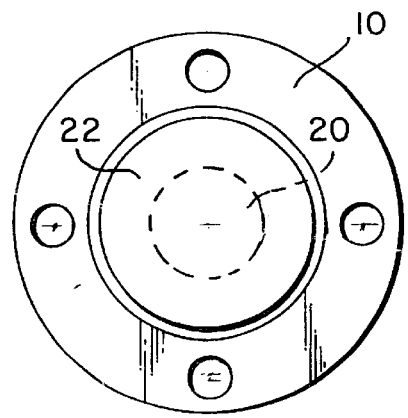
FIG. 4 is a top view of the tester of FIG. 3.

Referring now to FIGS. 3 and 4, the preferred embodiment of the strain rate tester according to the invention will be described. The tester includes a fixed base 10 having a vertical bore which contains a bolt 12 having a head 12a and a shaft 12b, the axis of which is arranged vertically. The bolt is used to mount a load cell 14 on the top of the base. The load cell has an annular configuration so that the shaft 12b passes therethrough. A suitable load cell is a Kistler Model 9011A. Between the load cell and the bolt shaft is a cylindrical alignment sleeve 16 which extends into the base 10 to assist in maintaining the bolt 12 in vertical alignment. A nut 18 is connected with the bottom of the bolt shaft to secure it and the load cell 14 in place.

The bolt head 12a serves as a lower platen for supporting a sample 20 of the material used in a sports ball. For ease of illustration, the sample is shown as having a rectangular configuration. However, the samples are not limited to a rectangular configuration and may in fact have any configuration. The sample is sandwiched between the bolt head and an upper platen 22. A striker 24, which provides the impact to the sample as a result of its mass $M_o$ and velocity $V_o$, is arranged above the base and dropped onto the top surface of the upper platen. Thus the momentum of the striker is delivered to the upper platen 22 in a downward vertical direction.

The reaction force from the sample at impact is detected by the load cell 14 to produce a force signal F(t). Deflection of the sample resulting from impact is detected by an optical detector 26 connected with the base 10. The optical detector produces a displacement signal L(t).

Any suitable displacement detector can be used in the tester according to the invention. One such detector is a fiber optic displacement sensor. Preferably, a plurality of such sensors are equally spaced around the base to direct a beam 28 against the lower surface of the upper platen 22. Thus, the upper platen is designed with an outer diameter greater than the diameter of the load cell and bolt head. The fiber optic sensors measure displacement of the upper platen in response to the impact on the sample.

The force F(t) and displacement L(t) signals are delivered to a processor 30 which is used to derive quantities for stress and strain of the sample from the force and displacement signals.

Figure 5:
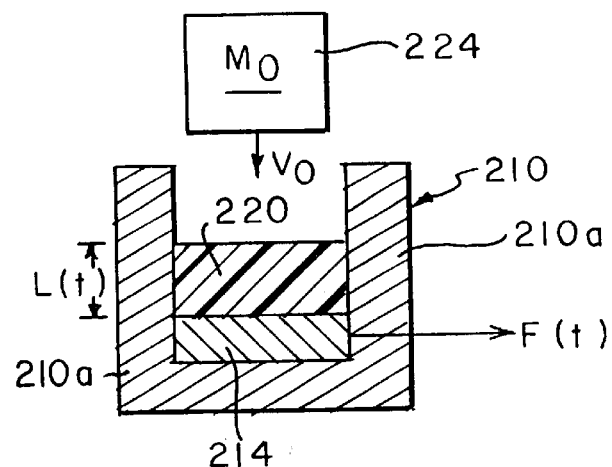
FIG. 5 is a sectional view of a second embodiment of a strain rate tester according to the invention.

A second embodiment of the invention will now be described with reference to FIG. 5. There, the base 210 includes a pair of spaced side walls 210a extending upwardly to define a channel. The base thus has a generally U-shaped configuration. A load cell 214 is arranged in the channel and extends between the side walls 210a. The sample 220 to be tested is arranged on the load cell and also extends between the base side walls, which serve to constrain the sample on two sides when the sample is under impact of a striker 224. The load cell measures the reactive force F(t) and a displacement detector (not shown) measures displacement L(t). Such an arrangement is useful for measuring shear because the sample is free to expand laterally out of one plane while being restricted in the other two planes.

Figure 6:
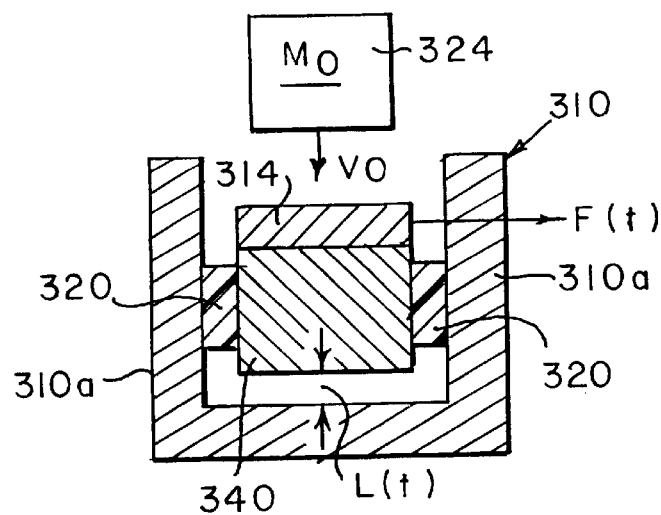
FIG. 6 is a sectional view of a third embodiment of a strain rate tester according to the invention.

An alternate arrangement for measuring shear is capable with the third embodiment shown in FIG. 6. The base 310 has side walls 310a to define a channel as in the embodiment of FIG. 5. Two samples 320, both of which are identical in size and composition, are mounted on interior surfaces of the side walls 310a, preferably by bonding with an adhesive. A block 340 is bonded between the opposing surfaces of the samples and suspended above the bottom of the base. In this embodiment, the samples have their major dimension extending vertically and their minor dimension extending horizontally as shown in FIG. 6. A load cell 314 is mounted on the top surface of the block 340. When the striker 324 is dropped onto the load cell 314, the load cell produces the reaction force signal F(t). Because the block and samples are suspended above the bottom of the base, and yet constrained by the base side walls, the samples are free to expand out of one plane, i.e. a vertical plane. The displacement L(t) of the samples is measured by a displacement detector (not shown).

Figure 7:
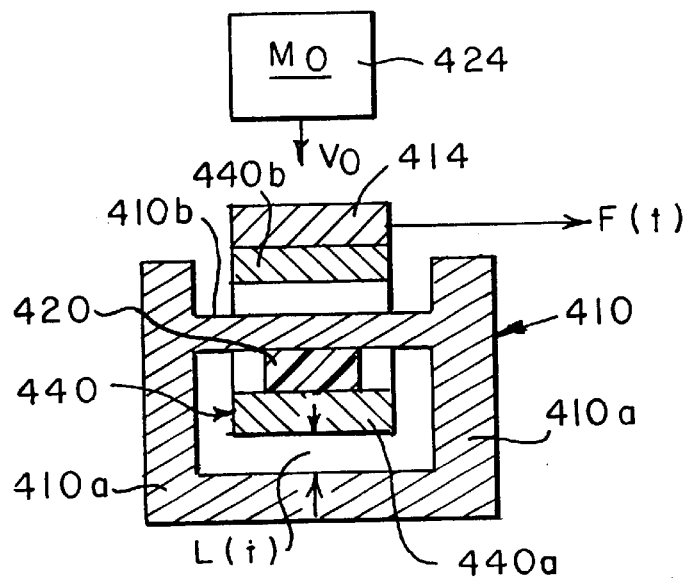
FIG. 7 is a sectional view of a fourth embodiment of a strain rate tester according to the invention.

A fourth embodiment which is useful for measuring tensile strain in a sample will be described with reference to FIG. 7. The base 410 has side walls 410a defining a channel and includes a top wall 410b extending between the side walls 410a. A sample 420 is bonded to the bottom surface of the top wall with its major dimension extending horizontally and its minor dimension extending vertically. A mounting block 440 straddles the top wall and has a lower portion 440*a* whose upper surface is bonded to the lower surface of the sample. An upper portion 440*b* of the mounting block is above the top wall and has a load cell 414 mounted thereon. With the arrangement shown in FIG. 7, the mounting block is suspended from the sample in spaced relation above the bottom of the base channel. When the striker 424 is dropped on the load cell, the cell produces the reaction force signal F(t). The displacement L(t) of the sample is not the result of compression as in the embodiments of FIGS. 3 and 5 but rather extension or deflection in the vertical direction. Thus, the displacement signal L(t) from a detector (not shown) is useful for providing an indication of tensile shear of the sample.

While the preferred forms and embodiments of the invention have been illustrated and described, it will be apparent to those of ordinary skill in the art that various changes and modifications may be made without deviating from the inventive concepts set forth above.

What is claimed is:

1. Apparatus for measuring strain rate of a sample of material used in sports balls, comprising:
    (1) a fixed base on which the sample is mounted;
    (2) a striker for delivering an impact to the sample in a first direction;
    (3) a first detector connected with said base for measuring the reaction force of the impact from the sample; and
    (4) a second detector connected with said base for measuring the displacement of the sample in said first direction, wherein said second detector comprises at least one optical detector, and further comprising means for mounting said sample on said base, wherein said mounting means comprises a lower platen connected with said base and an upper platen arranged on said sample, said sample being sandwiched between said upper and lower platens, wherein said lower platen comprises a bolt having a head portion supporting said sample and an axis colinear with a central axis of said striker and extending in said first direction, wherein said base has a U-shaped cross-sectional configuration to define a channel within which said sample is mounted, and further comprising a mounting block arranged in said channel and wherein said first detector comprises a load cell mounted on said mounting block, said mounting Block having a pair of samples connected with opposite surfaces thereof said pair of samples being further connected with adjacent side walls of said base, respectively, to suspend said block within said channel,
whereby said reaction force and said displacement is processed to determine the time dependent strain of the material.

2. Apparatus as defined in claim 1, wherein said impact delivered to said sample is variable in accordance with the momentum of said striker which produces said impact.

3. Apparatus as defined in claim 1, wherein said load cell has an annular configuration and is coaxially arranged about a shaft of said bolt below said head portion.

4. Apparatus as defined in claim 3, and further comprising a cylindrical alignment sleeve arranged between said bolt shaft and said load cell, said alignment sleeve extending into an opening in said base to maintain said sample mounting means and said load cell in alignment with said central axis of said striker.

5. Apparatus as defined in claim 1, wherein said optical detector directs a light beam against a bottom surface of said upper platen for measuring displacement of said upper platen in response to the impact on said sample.

6. Apparatus as defined in claim 5, wherein a plurality of optical detectors are connected with said base in spaced relation about a perimeter thereof for detecting displacement of said upper platen in a plurality of locations.

7. Apparatus as defined in claim 1, wherein said first detector comprises a load cell arranged in said channel and extending between side walls of said base, and said sample is arranged on said load cell and extends between said base side walls, whereby said sample is afforded lateral displacement toward open ends of said channel upon impact by said striker, said lateral displacement being detected as a measurement of strain of said sample normal to said first direction.

8. Apparatus as defined in claim 1, wherein said samples have a rectangular configuration and are of the same size and configuration, said samples being sandwiched between said block and said base side walls with a major dimension thereof being parallel to said first direction and a minor dimension thereof being normal to said first direction, whereby displacement of said samples is measured with respect to said major dimension.

9. Apparatus as defined in claim 8, wherein said samples are bonded to said block and to said side walls, respectively.

10. Apparatus as defined in claim 1, wherein said base includes a top wall extending between upper ends of said side walls, and further comprising a mounting block which straddles said top wall and wherein said first detector comprises a load cell mounted on said mounting block, said sample being connected with a lower surface of said base top wall and an upper surface of a lower portion of said mounting block, whereby said mounting block is suspended in said channel by said sample.

11. Apparatus as defined in claim 1, wherein said sample has a major dimension arranged normal to said first direction, said sample having top and bottom surfaces bonded to said base top wall and mounting block lower portion, respectively, whereby displacement of said sample is a function of tensile strain thereof.

12. Apparatus for measuring strain rate of a sample of material used in sports balls, comprising:
    (1) a fixed base on which the sample is mounted, further comprising means for mounting said sample on said base, wherein said base has a U-shaped cross-sectional configuration to define a channel within which said sample is mounted, and further comprising a mounting block arranged in said channel;
    (2) a striker for delivering an impact to the sample in a first direction;
    (3) a first detector connected with said base for measuring the reaction force of the impact from the sample, wherein said first detector comprises a load cell mounted on said mounting block, said mounting block having a pair of samples connected with opposite surfaces thereof, said pair of samples being further connected with adjacent side walls of said base, respectively, to suspend said block within said channel; and
    (4) a second detector connected with said base for measuring the displacement of the sample in said first direction, wherein said second detector comprises at least one optical detector, whereby said reaction force and said displacement is processed to determine the time dependent strain of the material.

13. Apparatus as defined in claim 12, wherein said samples have a retangular configuration and are of the same size, said samples being sandwiched between said block and said base side walls with a major dimension thereof being parallel to said first direction and a minor dimension thereof being normal to said first direction, whereby displacement of said samples is measured with respect to said major dimension.

14. Apparatus as defined in claim 13, wherein said samples are bonded to said block and to said side walls, respectively.

15. Apparatus as defined in claim 12, wherein said base includes a top wall extending between upper ends of said side walls, and further comprising a mounting block which straddles said top wall and wherein said first detector comprises a load cell mounted on said mounting block, said sample being connected with a lower surface of said base top wall and an upper surface of a lower portion of said mounting block, whereby said mounting block is suspended in said channel by said sample.

16. Apparatus as defined in claim 12, wherein said sample has a major dimension arranged normal to said first direction, said sample having top and bottom surfaces bonded to said base top wall and mounting block lower portion, respectively, whereby displacement of said sample is a function of tensile strain thereof.

\* \* \* \* \*